(12) United States Patent
Muhanna et al.

(10) Patent No.: US 8,066,773 B2
(45) Date of Patent: Nov. 29, 2011

(54) ARTIFICIAL INTERVERTEBRAL DISC

(75) Inventors: Nabil L. Muhanna, Gainesville, GA (US); Lance M. Middleton, Soddy Daisy, TN (US)

(73) Assignee: F3 Technologies, LLC, Scottsdale, AZ (US)

( * ) Notice: Subject to any disclaimer, the term of this patent is extended or adjusted under 35 U.S.C. 154(b) by 85 days.

(21) Appl. No.: 11/648,384

(22) Filed: Dec. 29, 2006

(65) Prior Publication Data

US 2007/0112429 A1 May 17, 2007

Related U.S. Application Data

(62) Division of application No. 10/766,684, filed on Jan. 28, 2004.

(51) Int. Cl.
*A61F 2/44* (2006.01)

(52) U.S. Cl. .................... 623/17.14; 623/17.15

(58) Field of Classification Search ..... 623/17.11–17.16
See application file for complete search history.

(56) References Cited

U.S. PATENT DOCUMENTS

| | | | |
|---|---|---|---|
| 3,030,951 A | 4/1962 | Mandarino | |
| 3,320,957 A | 5/1967 | Sokolik | |
| 3,867,728 A | 2/1975 | Stubstad et al. | |
| 3,875,595 A | 4/1975 | Froning | |
| 4,065,817 A | 1/1978 | Branemark et al. | |
| 4,309,777 A | 1/1982 | Patil | |
| 4,349,921 A | 9/1982 | Kuntz | |
| 4,369,772 A | 1/1983 | Miller | |
| 4,403,606 A | 9/1983 | Woo et al. | |
| 4,403,607 A | 9/1983 | Woo et al. | |
| 4,493,317 A | 1/1985 | Klaue | |
| 4,494,535 A | 1/1985 | Haig | |
| 4,503,848 A | 3/1985 | Caspar et al. | |
| 4,513,744 A | 4/1985 | Klaue | |
| 4,653,489 A | 3/1987 | Tronzo | |
| 4,743,260 A | 5/1988 | Burton | |
| 4,751,922 A | 6/1988 | DiPietropolo | |
| 4,759,766 A | 7/1988 | Buettner-Janz et al. | |
| 4,759,769 A | 7/1988 | Hedman et al. | |
| 4,773,406 A | 9/1988 | Spector et al. | |
| 4,794,918 A | 1/1989 | Wolter | |
| 4,863,477 A | 9/1989 | Monson | |
| 4,874,389 A | 10/1989 | Downey | |
| 4,911,718 A | 3/1990 | Lee et al. | |
| 4,932,975 A | 6/1990 | Main et al. | |
| 4,936,848 A | 6/1990 | Bagby | |
| 4,946,378 A | 8/1990 | Hirayama et al. | |

(Continued)

FOREIGN PATENT DOCUMENTS

DE 3914164 1/1991

(Continued)

OTHER PUBLICATIONS

U.S. Appl. No. 10/284,672, filed Oct. 31, 2002, Middleton.

*Primary Examiner* — Bruce E Snow

(57) ABSTRACT

An artificial intervertebral disc for at least partially replacing a diseased or damaged intervertebral disc. The artificial disc includes a concave-convex articulating surface. The artificial disc can be used in the cervical region of the spine, where a concave-convex articulating surface is advantageous for improved anatomical fit and region appropriate kinematics. The artificial disc of the present invention also includes an anchor for attachment to bone.

5 Claims, 12 Drawing Sheets

U.S. PATENT DOCUMENTS

| | | | |
|---|---|---|---|
| 4,969,888 | A | 11/1990 | Scholten et al. |
| 5,002,544 | A | 3/1991 | Klaue et al. |
| 5,002,576 | A | 3/1991 | Fuhrmann et al. |
| 5,019,078 | A | 5/1991 | Perren et al. |
| 5,030,201 | A | 7/1991 | Palestrant |
| 5,035,716 | A | 7/1991 | Downey |
| 5,053,036 | A | 10/1991 | Perren et al. |
| 5,062,845 | A | 11/1991 | Kuslich et al. |
| 5,071,437 | A | 12/1991 | Steffee |
| 5,085,660 | A | 2/1992 | Lin |
| 5,108,404 | A | 4/1992 | Scholten et al. |
| 5,108,438 | A | 4/1992 | Stone |
| 5,118,338 | A | 6/1992 | Moller |
| 5,123,926 | A | 6/1992 | Pisharodi |
| 5,147,361 | A | 9/1992 | Ojima et al. |
| 5,151,103 | A | 9/1992 | Tepic et al. |
| 5,171,281 | A | 12/1992 | Parsons et al. |
| 5,246,458 | A | 9/1993 | Graham |
| 5,258,031 | A | 11/1993 | Salib et al. |
| 5,275,601 | A | 1/1994 | Gogolewski et al. |
| 5,314,477 | A | 5/1994 | Marnay |
| 5,320,644 | A | 6/1994 | Baumgartner |
| 5,344,421 | A | 9/1994 | Crook |
| 5,364,399 | A | 11/1994 | Lowery et al. |
| 5,370,697 | A | 12/1994 | Baumgartner |
| 5,376,100 | A | 12/1994 | Lefebvre |
| 5,401,269 | A | 3/1995 | Buttner-Janz et al. |
| 5,403,136 | A | 4/1995 | Mathys |
| 5,403,317 | A | 4/1995 | Bonutti |
| 5,425,773 | A | 6/1995 | Boyd et al. |
| 5,431,671 | A | 7/1995 | Nallakrishnan |
| 5,445,639 | A | 8/1995 | Kuslich et al. |
| 5,458,642 | A | 10/1995 | Beer et al. |
| 5,458,643 | A | 10/1995 | Oka et al. |
| 5,514,137 | A | 5/1996 | Coutts |
| 5,514,180 | A | 5/1996 | Heggeness et al. |
| 5,527,311 | A | 6/1996 | Procter et al. |
| 5,534,029 | A | 7/1996 | Shima |
| 5,545,229 | A | 8/1996 | Parsons et al. |
| 5,549,612 | A | 8/1996 | Yapp et al. |
| 5,556,429 | A | 9/1996 | Felt |
| 5,562,672 | A | 10/1996 | Huebner et al. |
| 5,562,738 | A | 10/1996 | Boyd et al. |
| 5,607,426 | A | 3/1997 | Ralph et al. |
| 5,613,967 | A | 3/1997 | Engelhardt et al. |
| 5,616,144 | A | 4/1997 | Yapp et al. |
| 5,645,596 | A | 7/1997 | Kim et al. |
| 5,645,605 | A | 7/1997 | Klawitter |
| 5,658,310 | A | 8/1997 | Berger |
| 5,665,110 | A | 9/1997 | Chervitz et al. |
| 5,674,294 | A | 10/1997 | Bainville et al. |
| 5,674,296 | A | 10/1997 | Bryan et al. |
| 5,681,310 | A | 10/1997 | Yuan et al. |
| 5,681,311 | A | 10/1997 | Foley et al. |
| 5,693,011 | A | 12/1997 | Onik |
| 5,695,513 | A | 12/1997 | Johnson et al. |
| 5,709,686 | A | 1/1998 | Talos et al. |
| 5,720,749 | A | 2/1998 | Rupp |
| 5,733,287 | A | 3/1998 | Tepic et al. |
| 5,735,853 | A | 4/1998 | Olerud |
| 5,766,176 | A | 6/1998 | Duncan |
| 5,772,662 | A | 6/1998 | Chapman et al. |
| 5,782,832 | A | 7/1998 | Larsen et al. |
| 5,800,433 | A | 9/1998 | Benzel et al. |
| 5,807,396 | A | 9/1998 | Raveh |
| 5,824,094 | A | 10/1998 | Serhan et al. |
| 5,827,289 | A | 10/1998 | Reiley et al. |
| 5,827,328 | A | 10/1998 | Buttermann |
| 5,843,103 | A | 12/1998 | Wulfman |
| 5,865,846 | A | 2/1999 | Bryan et al. |
| 5,871,486 | A | 2/1999 | Huebner et al. |
| 5,888,220 | A | 3/1999 | Felt et al. |
| 5,888,226 | A | 3/1999 | Rogozinski |
| 5,891,145 | A | 4/1999 | Morrison et al. |
| 5,893,889 | A | 4/1999 | Harrington |
| 5,899,941 | A | 5/1999 | Nishijima et al. |
| 5,904,683 | A | 5/1999 | Pohndorf et al. |
| 5,925,056 | A | 7/1999 | Thomas et al. |
| 5,928,239 | A | 7/1999 | Mirza |
| 5,928,284 | A | 7/1999 | Mehdizadeh |
| 5,935,131 | A | 8/1999 | Bonutti |
| 5,935,853 | A | 8/1999 | Jones et al. |
| 5,964,762 | A | 10/1999 | Biedermann et al. |
| 5,972,015 | A | 10/1999 | Scribner et al. |
| 5,990,194 | A | 11/1999 | Dunn et al. |
| 6,017,345 | A | 1/2000 | Richelsoph |
| 6,019,792 | A | 2/2000 | Cauthen |
| 6,022,350 | A | 2/2000 | Ganem |
| 6,030,389 | A | 2/2000 | Wagner et al. |
| 6,039,763 | A | 3/2000 | Shelokov |
| 6,048,343 | A | 4/2000 | Mathis et al. |
| 6,063,121 | A | 5/2000 | Xavier et al. |
| 6,066,154 | A | 5/2000 | Reiley et al. |
| 6,071,284 | A | 6/2000 | Fox |
| 6,113,637 | A | 9/2000 | Gill et al. |
| 6,136,031 | A | 10/2000 | Middleton |
| 6,139,509 | A | 10/2000 | Yuan et al. |
| 6,140,452 | A | 10/2000 | Felt et al. |
| 6,156,067 | A | 12/2000 | Bryan et al. |
| 6,171,312 | B1 | 1/2001 | Beaty |
| 6,179,874 | B1 | 1/2001 | Cauthen |
| 6,210,376 | B1 | 4/2001 | Grayson |
| 6,214,012 | B1 | 4/2001 | Karpman et al. |
| 6,224,604 | B1 | 5/2001 | Suddaby |
| 6,235,043 | B1 | 5/2001 | Reiley et al. |
| 6,238,391 | B1 | 5/2001 | Olsen et al. |
| 6,241,734 | B1 | 6/2001 | Scribner et al. |
| 6,248,110 | B1 | 6/2001 | Reiley et al. |
| 6,248,131 | B1 | 6/2001 | Felt et al. |
| 6,264,659 | B1 | 7/2001 | Ross et al. |
| 6,296,639 | B1 | 10/2001 | Truckai et al. |
| 6,383,188 | B2 | 5/2002 | Kuslich et al. |
| 6,410,452 | B2 | 6/2002 | Nishioka |
| 6,440,138 | B1 | 8/2002 | Reiley et al. |
| 6,527,804 | B1 | 3/2003 | Gauchet et al. |
| 6,558,386 | B1 | 5/2003 | Cragg |
| 6,558,390 | B2 | 5/2003 | Cragg |
| 6,575,979 | B1 | 6/2003 | Cragg |
| 6,607,558 | B2 | 8/2003 | Kuras |
| 6,706,068 | B2 | 3/2004 | Ferree |
| 6,740,090 | B1 | 5/2004 | Cragg et al. |
| 6,770,094 | B2 | 8/2004 | Fehling et al. |
| 6,770,095 | B2 | 8/2004 | Grinberg et al. |
| 6,790,210 | B1 | 9/2004 | Cragg et al. |
| 6,899,716 | B2 | 5/2005 | Cragg |
| 6,921,403 | B2 | 7/2005 | Cragg et al. |
| 2001/0021852 | A1 | 9/2001 | Chappius |
| 2001/0049527 | A1 | 12/2001 | Cragg |
| 2002/0016583 | A1 | 2/2002 | Cragg |
| 2002/0116064 | A1 | 8/2002 | Middleton |
| 2002/0173796 | A1 | 11/2002 | Cragg |
| 2003/0135237 | A1 | 7/2003 | Cragg et al. |
| 2003/0158557 | A1 | 8/2003 | Cragg et al. |
| 2003/0191474 | A1 | 10/2003 | Cragg et al. |
| 2003/0195518 | A1 | 10/2003 | Cragg |
| 2003/0204189 | A1 | 10/2003 | Cragg |
| 2003/0229353 | A1 | 12/2003 | Cragg |
| 2004/0024462 | A1 | 2/2004 | Ferree et al. |
| 2004/0176772 | A1 | 9/2004 | Zubok et al. |
| 2004/0176773 | A1 | 9/2004 | Zubok et al. |
| 2004/0176774 | A1 | 9/2004 | Zubok et al. |
| 2004/0176776 | A1 | 9/2004 | Zubok et al. |
| 2004/0176777 | A1 | 9/2004 | Zubok et al. |
| 2004/0176778 | A1 | 9/2004 | Zubok et al. |
| 2004/0176843 | A1 | 9/2004 | Zubok et al. |
| 2004/0176844 | A1 | 9/2004 | Zubok et al. |
| 2004/0176845 | A1 | 9/2004 | Zubok et al. |
| 2004/0176846 | A1 | 9/2004 | Zubok et al. |
| 2004/0176847 | A1 | 9/2004 | Zubok et al. |
| 2004/0176848 | A1 | 9/2004 | Zubok et al. |
| 2004/0176849 | A1 | 9/2004 | Zubok et al. |
| 2004/0176850 | A1 | 9/2004 | Zubok et al. |
| 2004/0176851 | A1 | 9/2004 | Zubok et al. |
| 2004/0176852 | A1 | 9/2004 | Zubok et al. |
| 2004/0193272 | A1 | 9/2004 | Zubok et al. |
| 2004/0220577 | A1 | 11/2004 | Cragg et al. |
| 2004/0220590 | A1 | 11/2004 | Zubok et al. |

| | | |
|---|---|---|
| 2005/0070908 A1 | 3/2005 | Cragg |
| 2005/0071013 A1 | 3/2005 | Zubok et al. |
| 2005/0113919 A1 | 5/2005 | Cragg et al. |
| 2005/0113928 A1 | 5/2005 | Cragg et al. |
| 2005/0113929 A1 | 5/2005 | Cragg et al. |
| 2005/0131529 A1 | 6/2005 | Cragg |
| 2005/0137601 A1 | 6/2005 | Assell et al. |
| 2005/0137602 A1 | 6/2005 | Assell et al. |
| 2005/0137604 A1 | 6/2005 | Assell et al. |
| 2005/0137605 A1 | 6/2005 | Assell et al. |
| 2005/0137607 A1 | 6/2005 | Assell et al. |
| 2005/0137612 A1 | 6/2005 | Assell et al. |
| 2005/0149034 A1 | 7/2005 | Assell et al. |
| 2005/0149049 A1 | 7/2005 | Assell et al. |
| 2005/0149191 A1 | 7/2005 | Cragg et al. |
| 2005/0165406 A1 | 7/2005 | Assell et al. |
| 2005/0187633 A1 | 8/2005 | Ferree |
| 2005/0240271 A1 | 10/2005 | Zubok et al. |
| 2005/0240272 A1 | 10/2005 | Zubok et al. |
| 2005/0256577 A1 | 11/2005 | Baumgartner et al. |
| 2005/0261695 A1 | 11/2005 | Cragg et al. |

FOREIGN PATENT DOCUMENTS

| | | |
|---|---|---|
| EP | 0 442 137 B1 | 8/1991 |
| WO | WO-9007304 | 7/1990 |
| WO | WO-98/51226 A2 | 11/1998 |
| WO | WO-98/51226 A3 | 11/1998 |
| WO | 99/11203 * | 3/1999 |

* cited by examiner

ARTIFICIAL INTERVERTEBRAL DISC

CROSS REFERENCE TO RELATED APPLICATIONS

This application is a divisional of U.S. patent application Ser. No. 10/766,684 filed on Jan. 28, 2004.

FIELD OF THE INVENTION

The present invention generally relates to an apparatus for the treatment of spinal disorders and, in particular, an artificial intervertebral disc, an implant that replaces a diseased or damaged intervertebral disc.

BACKGROUND OF THE INVENTION

There are many painful disorders of the spine, many relating, at least in part, to diseased or damaged intervertebral discs. Disorders include Degenerative Disc Disease, generally an age related disorder where the intervertebral disc gradually loses its water content, resiliency, and height. With a loss in intervertebral disc height and associated loss of normal spacing between vertebrae, motion of the vertebrae can place pressure on the spinal cord or exiting nerve roots. The intervertebral disc itself can also be a source of pain. Spinal disorders, commonly referred to as disc herniation and bulging disc, place painful pressure on the spinal cord and exiting nerve roots. Abnormal bone growth, called osteophytes, can place pressure on nerves or the spinal cord. Often, a surgeon must at least partially remove an intervertebral disc to access and remove an osteophyte.

A surgical approach to treating chronic spinal disorders relates to bony fusion of two adjacent vertebrae in a treatment called spine fusion. Following the achievement of appropriate spacing and alignment of the vertebral bodies, bone graft material and stabilization provide an environment for spine fusion. Implant systems, to include plate and rod systems and interbody devices, such as, interbody spacers and fusion cages can be used to support the spine during fusion. Concerns persist regarding spinal fusion treatment stemming from modest clinical success rates and the creation of rigid regions along an otherwise flexible spine.

Artificial intervertebral discs, or simply artificial discs, are an alternative to spinal fusion and represent an emerging technology. These spinal implants are designed to restore or maintain the appropriate alignment and spacing of adjacent vertebral bodies. In addition, an artificial disc is also designed for kinematic behavior similar to a healthy natural disc. Known artificial disc concepts use numerous means for providing motion and stiffness similar to a natural healthy disc, to include the adaptation of elastomers, mechanical springs, and articulating surfaces.

Prior art artificial discs often use articulating surfaces to create a joint between adjacent vertebrae. Disc implants using articulating surfaces rely on methodology and proven technology used in total joint arthroplasty of the hip, knee, and shoulder. Numerous prior art artificial discs resemble artificial hip and artificial knee joints. Numerous known artificial disc devices resemble variations of a ball-and-socket. Kuntz, in U.S. Pat. No. 4,349,921 (Sep. 21, 1982) discloses an artificial disc, with two components that articulate by means of a projection on one component pivotally engaging a depression on the second component. An artificial disc resembling an artificial knee joint has also been suggested. Shelokov, in U.S. Pat. No. 6,039,763 (Mar. 21, 2000) discloses an artificial spinal disc, similar in configuration to an artificial knee joint.

Heggeness et. al., in U.S. Pat. No. 5,514,180 (May 1996) categorizes the shape or contours of vertebral endplates into five groups: "ramp", "saddle", "irregular", "bowl", and "hump". Heggeness et. al., teaches the importance of endplate shape relating to fit and load distribution of a prosthetic devices within intervertebral disc spaces, but Heggeness et. al. does not discuss endplate shape relating to articulating surfaces or spinal kinematics.

Spine kinematics and anatomical shapes vary by region of the spine (cervical, thoracic, and lumbar), and a need exists for artificial discs addressing specific regions of the spine, especially the unique geometry and kinematics of the cervical spine.

SUMMARY OF THE INVENTION

For the middle and lower regions of the cervical spine, the artificial disc of the present invention adapts an articulating surface with a concave-convex shape, also called a saddle shape. The artificial disc of the present invention is intended to fit substantially within the intervertebral space bound by adjacent vertebral bodies. A bone anchor for fixation of an artificial disc to vertebra is also disclosed.

A first embodiment of the artificial disc of the present invention for the cervical spine includes a disc body having an articulating concave-convex surface secured to a base plate, which may incorporate a bone anchor. A second embodiment of the artificial disc of the present invention is comprised of an articulating concave-convex surface, bone anchor, and a disc body slidably attached to a base plate to permit additional motion. A third embodiment of the artificial disc of the present invention includes an upper disc body and a lower disc body cooperatively forming a saddle-joint. The upper disc body and lower disc body of the third embodiment are securely anchored to vertebral bodies using bone anchors. Further embodiments of the artificial disc of the present invention include an upper disc body and a lower disc body cooperatively forming a saddle-joint, and bone anchors adapted with a tension element to provide additional stability.

DETAILED DESCRIPTION

Consistent with common medical nomenclature, superior is nearer the head in relation to a specific reference point, whereas, inferior is nearer the feet in relation to a specific reference point. Anterior is forward in relation to a specific reference point and posterior is rearward in relation to a specific reference point. The midsagittal plane is an imaginary plane dividing the body into a right side and left side. A frontal plane is any imaginary vertical plane orthogonal to the midsagittal plane.

Figure 1:
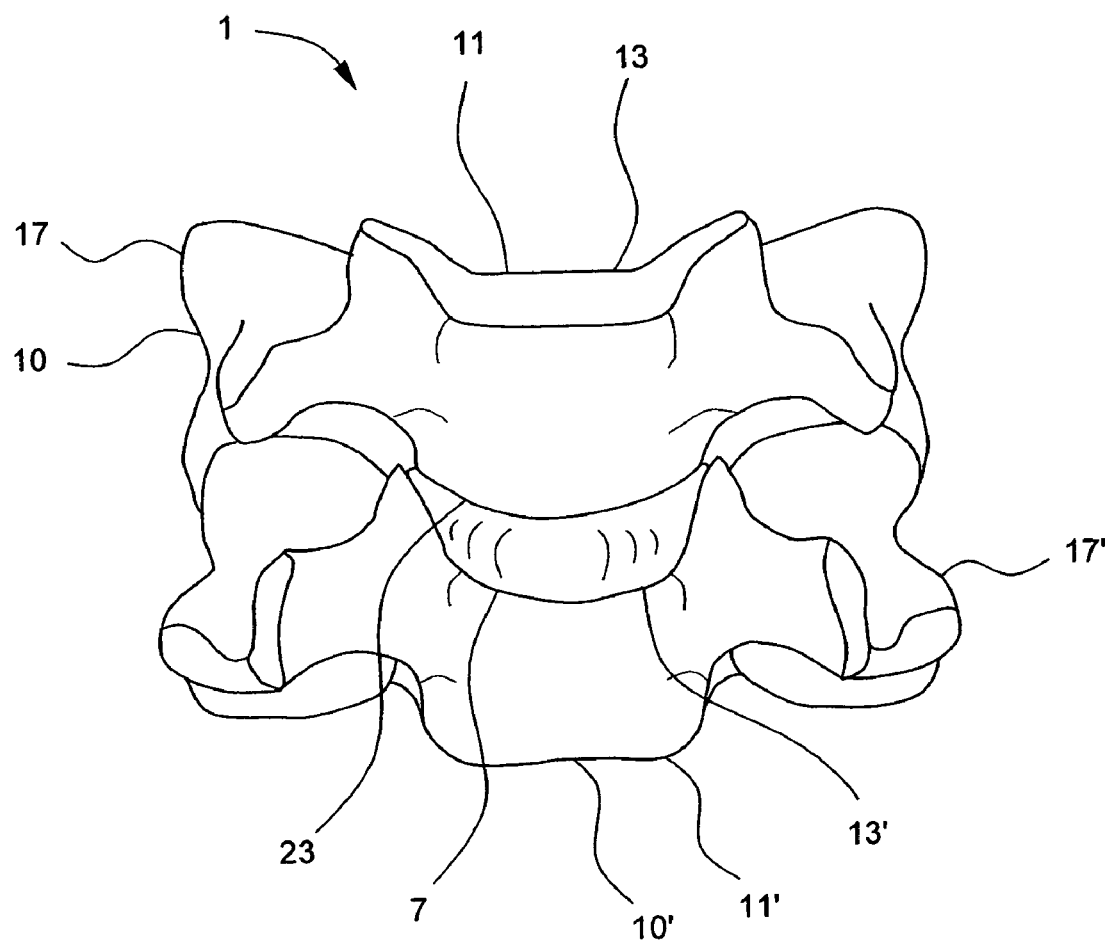
FIG. 1 shows a frontal view of a cervical spine motion segment comprised of two vertebrae and an intervertebral disc.

FIG. 1 shows a cervical spinal motion segment 1 characteristic of the middle and lower cervical spine comprised of a superior vertebra 10, an intervertebral disc 7, and an inferior vertebra 10'. Superior vertebra 10 is divided into two regions to include superior vertebral body 11 and superior posterior elements 17. Similarly, inferior vertebra 10' is divided into two regions to include inferior vertebral body 11' and inferior posterior elements 17'. Although separated by the intervertebral disc 7 to permit motion, the superior vertebral body 11 and the inferior vertebral body 11' are anatomically interlocking due to the reciprocal reception of the generally saddle-shaped inferior endplate 23 of the superior vertebral body 11 with the superior endplate 13' of inferior vertebral body 11'. Although the spinal motion segments are not a synovial joint, the most closely related synovial joint to the middle and lower cervical spine motion segments is the carpometacarpal joint of the thumb, which is formed by articulating surfaces in the form of a saddle-joint. In contrast, the vertebral bodies of other regions of the spine (thoracic and lumbar) are not anatomically interlocking.

Figure 2A:
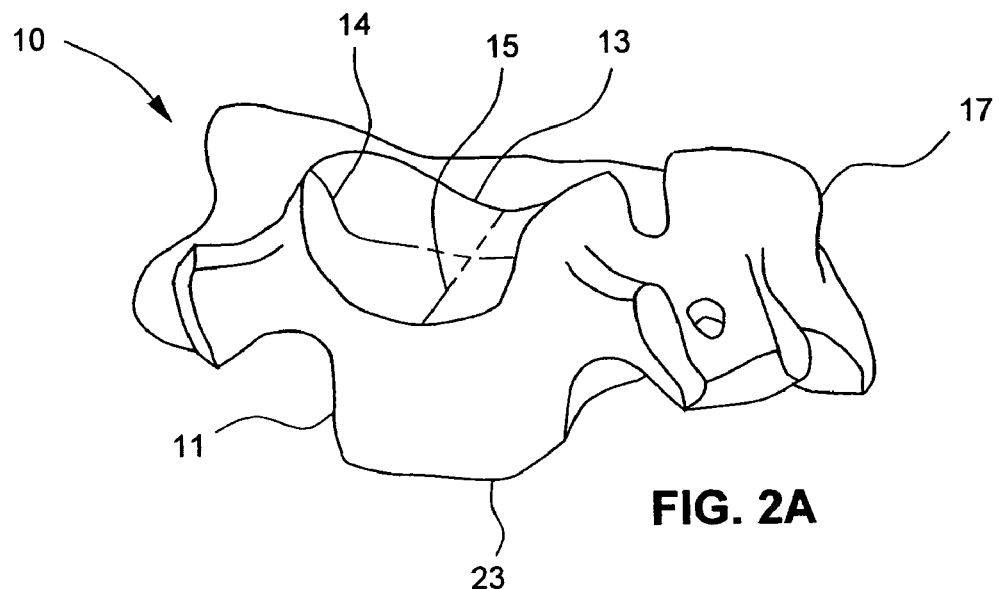
FIG. 2A shows a cervical vertebra in a perspective view of the superior endplate.
Figure 2B:
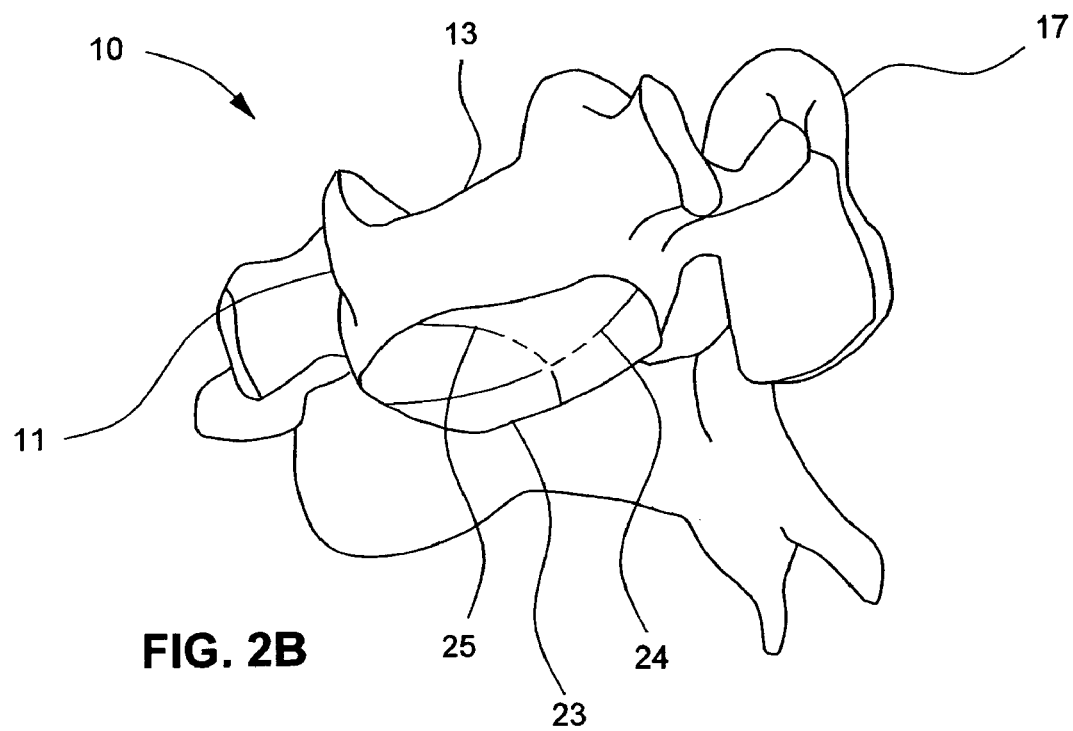
FIG. 2B shows an alternate perspective view of the cervical vertebra shown in FIG. 1A to emphasize the inferior endplate.

FIG. 2A and FIG. 2B show cervical vertebra 10 of FIG. 1 viewed at different perspectives to highlight superior endplate 13 and inferior endplate 23, respectively. Consistent with established medical nomenclature, cervical vertebra 10 includes vertebral body 11, and the bony structures attached to vertebral body 11 are posterior elements 17. The superior endplate 13 is generally concave, or at least partially concave, as indicated by the superior frontal surface line 14. The superior midsagittal surface line 15 is substantially straight but may be slightly concave or convex, or at least partially concave or convex. The inferior concave-convex endplate 23 is substantially convex in the medial-lateral direction and substantially concave in the anterior/posterior direction to form a saddle surface, as indicated by inferior convex surface line 24 and inferior concave surface line 25.

Figure 3:
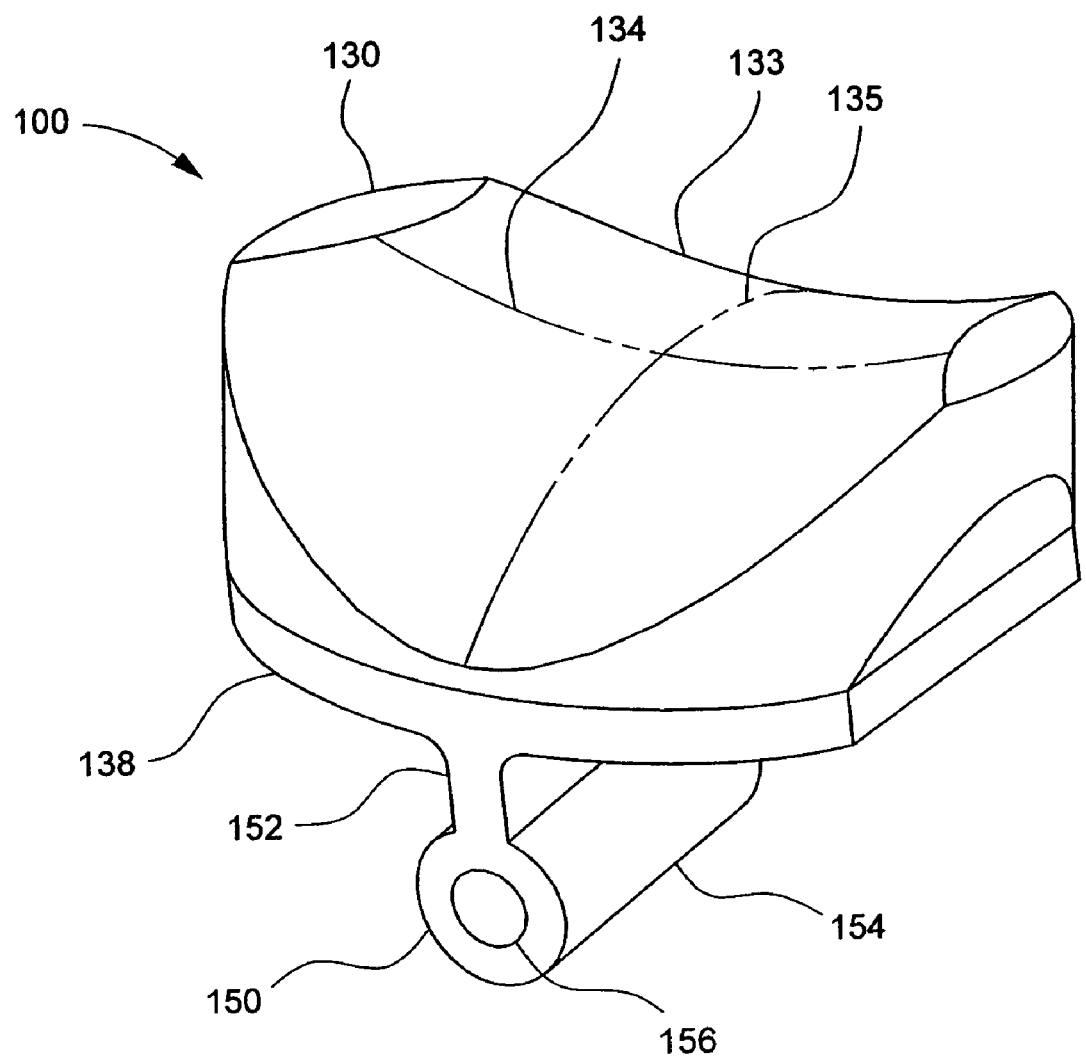
FIG. 3 shows a first preferred embodiment artificial disc of the present invention for the cervical spine with an articulating concave-convex surface.
Figure 4C:
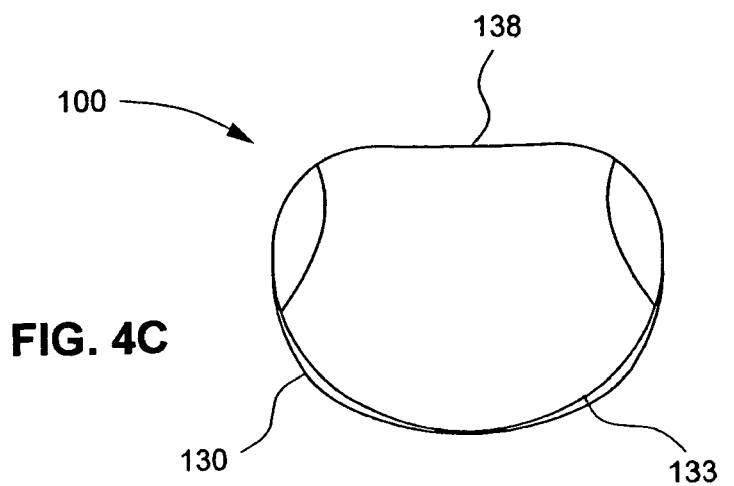
FIG. 4A, FIG. 4B, and FIG. 4C show the artificial disc depicted in FIG. 3 in orthogonal views to include a front view, side view, and top view, respectively.
Figure 4B:
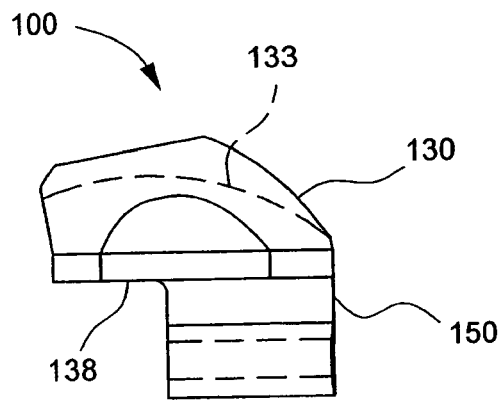
Figure 4A:
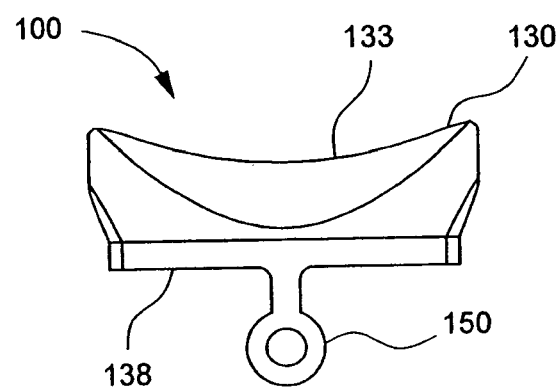
Figure 5:
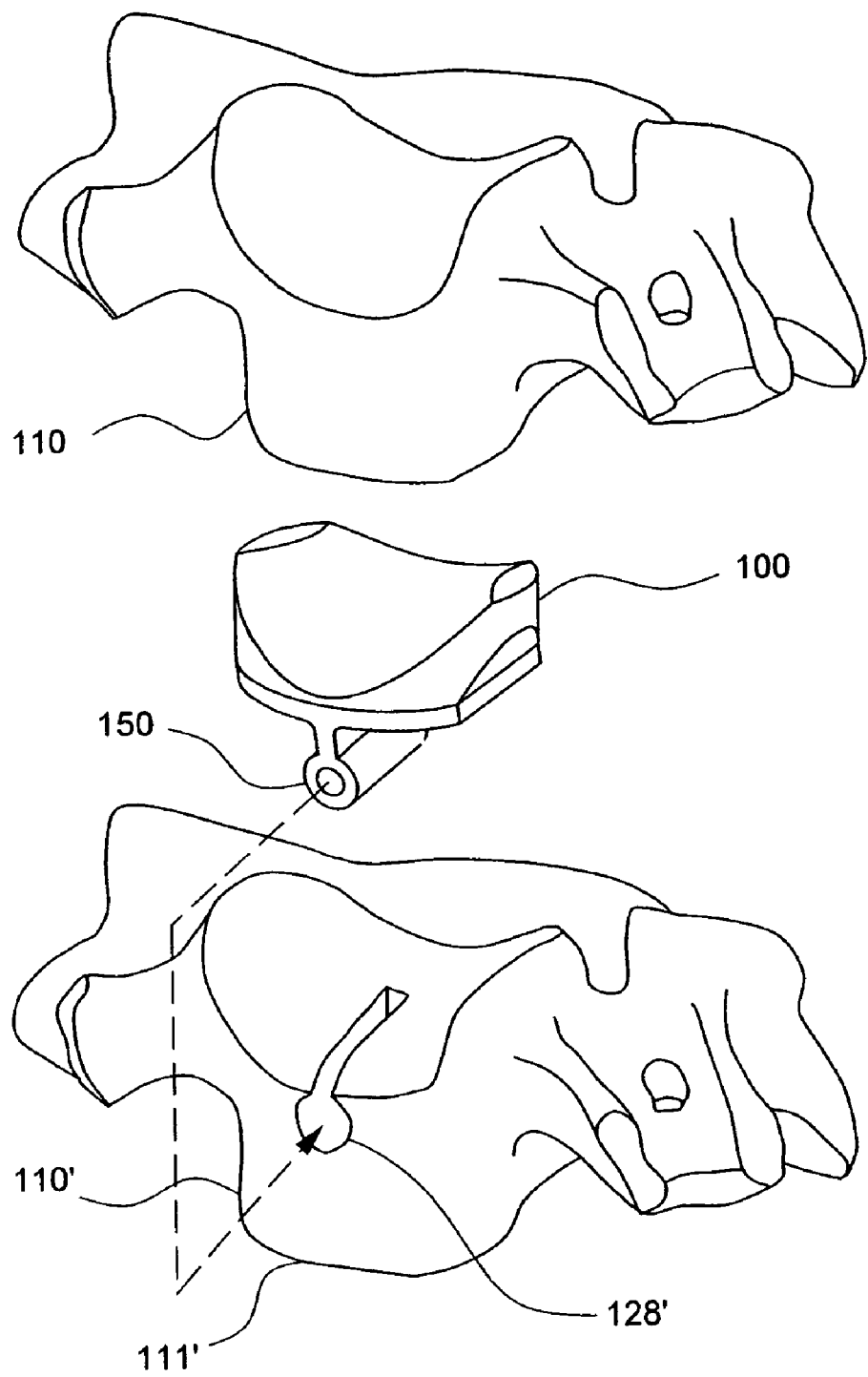
FIG. 5 shows the artificial disc depicted in FIG. 3 in an exploded view to include adjacent vertebrae of the cervical spine.

Primarily addressing the middle and lower cervical spine, the present invention uses a generally concave-convex articulating surface. As will become apparent in subsequent discussion, a concave-convex articulating surface is an essential element of the present invention, providing anatomical and biomechanical advantages. Referring now to FIG. 3, a first preferred embodiment, artificial disc 100, is comprised of a disc body 130, base plate 138, and bone anchor 150. Concave-convex articulating surface 133 is further revealed by considering two example reference lines formed from convenient planer reference planes, concave surface line 134 and midsagittal convex surface line 135. The curvature of concave-convex articulating surface 133 may be formed of simple radii or variable radii, and may be further expressed mathematically, at least in part, as a hyperbolic paraboloid, saddle-surface, or surface with negative curvature As will become apparent in subsequent discussion, a concave-convex articulating surface is an essential element of the present invention, providing anatomical and biomechanical advantages. Disc body 130 and base plate 138 are shown as separate components, although manufacture as a single component is also contemplated. Disc body 130 has a height appropriate for spacing of the vertebral bodies and may be of various shapes and sizes in order to substantially fill the surgically prepared space between vertebral bodies. Base plate 138 may have planer surfaces and uniform thickness, as shown in FIG. 3, although variable thickness and curved surfaces are also contemplated. Bone anchor 150 and base plate 138 are adapted for fixation to bone. Bone anchor 150 is comprised of vertical anchor web 152, anchor body 154, and anchor hole 156. As shown in FIG. 3, vertical anchor web 152 has a vertical height greater than width. In addition, vertical anchor web 152 may take other various forms, to include, but not be limited to, a web with variable thickness. Anchor body 154 is a protuberance with a width substantially greater than the thickness of vertical anchor web 152. As shown in FIG. 3, anchor body 154 is cylindrical, but other shapes are also contemplated, to include, but not limited to, a box shape. A use of anchor hole 156 is to releasably attach a surgical instrument during insertion of artificial disc 100. FIG. 4A, FIG. 4B, and FIG. 4C show artificial disc 100 in orthogonal views to include a front view, side view, and top view, respectively FIG. 5 shows the first preferred embodiment artificial disc 100 of the present invention depicted in FIG. 3 in an exploded perspective view between superior cervical vertebra 110 and inferior cervical vertebra 110'. Inferior vertebral body 111' includes a surgically created vertebral body key-hole 128' intended to receive bone anchor 150. Bone anchor 150 provides secure interlocking fixation with inferior vertebral body 111' and requires a minimal amount of bone removal.

Figure 6:
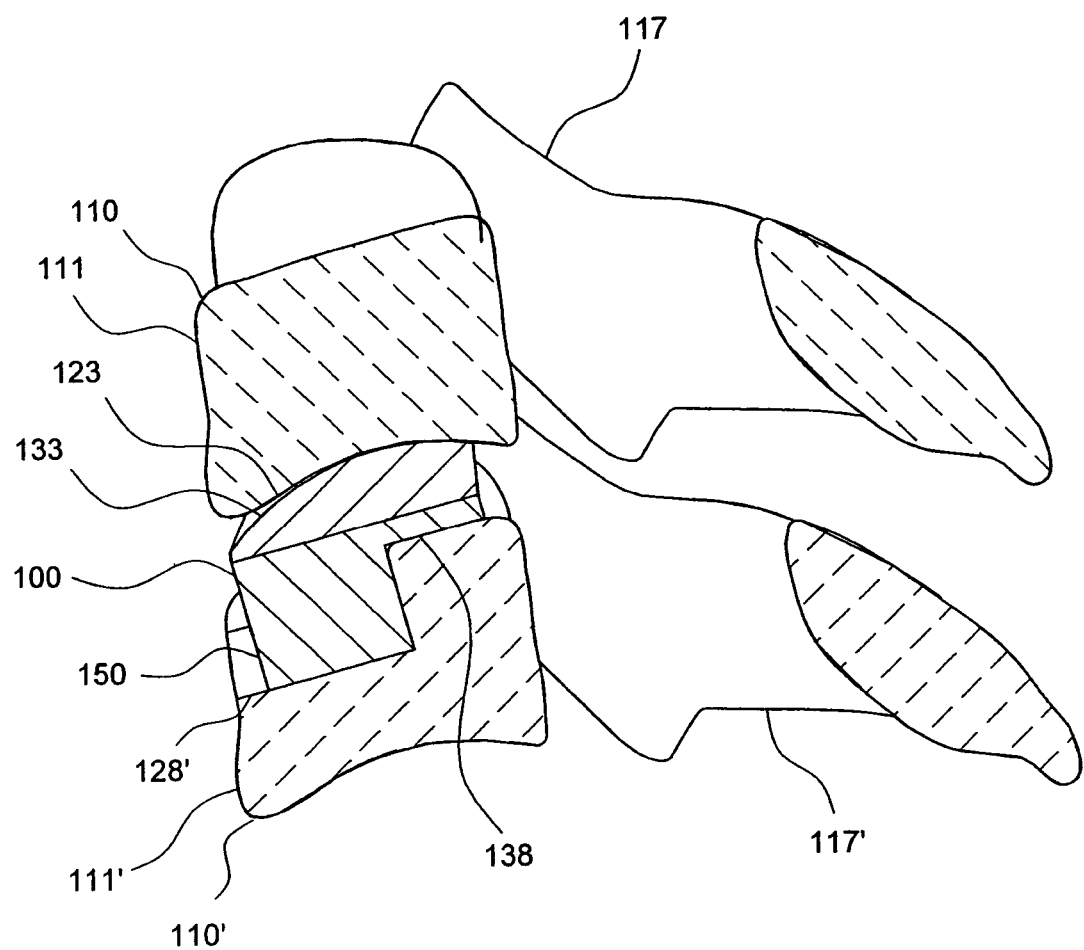
FIG. 6 shows a midsagittal sectional view of the first preferred embodiment artificial disc of the present invention depicted in FIG. 3 between adjacent cervical vertebrae.

FIG. 6 shows a midsagittal sectional view of the first preferred embodiment artificial disc 100 depicted in FIG. 3 between superior cervical vertebra 110 and inferior cervical vertebra 110'. Superior vertebra 110 is comprised of superior vertebral body 111 and superior posterior elements 117. Similarly, inferior vertebra 110' is divided into two regions to include inferior vertebral body 111' and inferior posterior elements 117'. Concave-convex articulating surface 133 is intended to slide with respect to inferior concave-convex endplate 123 provided the cartilaginous inferior concave-convex endplate 123 remains substantially intact following treatment of the patient's pathology. The contour of concave-convex articulating surface 133 is substantially similar to the contour of inferior concave-convex endplate 123, although some mismatch and variability is expected. It is expected that a patient's endplate can modify and generally adapt to the shape of an implant during healing. Bone anchor 150 is positioned within vertebral body key-hole 128'. Base plate 138 may have additional features for bony in-growth into inferior vertebral body 111' through the use of established porous materials or surface treatments. The anatomically aligned shape of artificial disc 100 results in a near complete fill of the intervertebral disc space; the resulting construct is substantially free of large voids that are potentially susceptible to eventual tissue encroachment. Significant tissue encroachment into an artificial disc could potentially interfere with movement of an artificial disc. Finally, the anatomically aligned shape of artificial disc 100 is intended to fit within the intervertebral disc space with minimal bone removal and endplate preparation during surgery, reducing surgical time and preserving otherwise healthy tissue.

The anatomically aligned shape of the present invention also has biomechanical benefits associated with natural kinematics of the spine. To assist with the analysis of spine kinematics, Panjabi and White established the Instantaneous-Axis-of-Rotation (IAR) for planer motion analysis of vertebrae. Planar motion of vertebrae is fully described by the position of the IAR and the angle of rotation about the IAR. The IAR is an instantaneous measure and therefore may shift within a region through a range-of-motion, such as, but not limited to, flexion/extension range-of-motion. The present inventors have discovered a relation between the shape of a vertebra's inferior endplate and the natural motion of the same vertebra.

Figure 7:
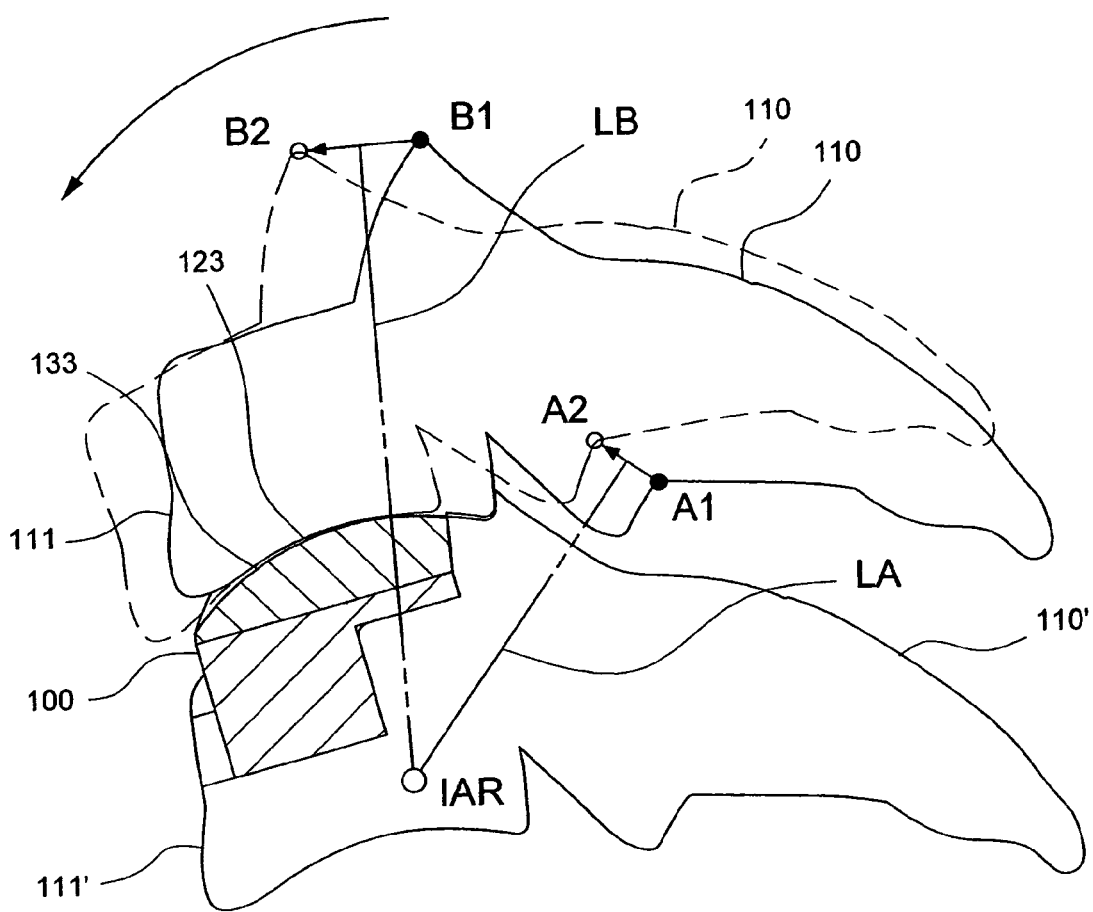
FIG. 7 shows a midsagittal sectional view of a first preferred embodiment artificial disc of the present invention depicted in FIG. 3 with a schematic of Instantaneous-Axis-of-Rotation (IAR) of a superior vertebra in flexion.

Flexion/extension is the most commonly considered degree-of-freedom when evaluating cervical spine kinematics. FIG. 7 shows the first preferred embodiment, artificial disc 100 depicted in FIG. 3, in a midsagittal sectional view between superior vertebra 110 and inferior vertebra 110'. Superior vertebra 110 is shown in a neutral position with locator point A1 and locator point B1 and in a flexed position with locator point A2 and locator point B2. Locator points may be any two unique points on a vertebra, and convenient anatomical landmarks are often used for these reference points. The selected frame of reference is inferior vertebra 110', so the instantaneous-axis-of-rotation IAR is of superior vertebra 110 with respect to inferior vertebrae 110'. Continuing to refer to FIG. 7, instantaneous-axis-of-rotation IAR is established by determining the intersection of line LA and line LB, where line LA and line LB are bisected normal lines of translation vector A1A2 and translation vector B1B2, respectively. Concave-convex articulating surface 133 has been adapted to have a substantially similar shape to inferior concave-convex endplate 123. Continuing to refer to FIG. 7, inferior concave-convex endplate 123 sliding with respect to concave-convex articulating surface 133 establishes the motion in flexion. The general region of Instantaneous-Axis-of-Rotation IAR is within the posterior region of inferior vertebral body 111'. Concerning the middle and lower cervical spine, the Instantaneous-Axis-of-Rotation IAR in flexion/extension of artificial disc 100, shown in FIG. 7, is consistent with recent scientific research demonstrating the IAR of a superior vertebra in flexion/extension generally lay within a posterior region of an inferior vertebral body (DiAngelo et. al., proceedings of Cervical Spine Research Society Meeting 2000). Further, the mathematical equations defining the shape of concave-convex articulating surface 133, generally in the form of a hyperbolic paraboloid, can be developed to substantially replicate the complex natural motions of the spine, to include, but not limited to, flexion/extension, lateral bending, and torsional motion.

Figure 8:
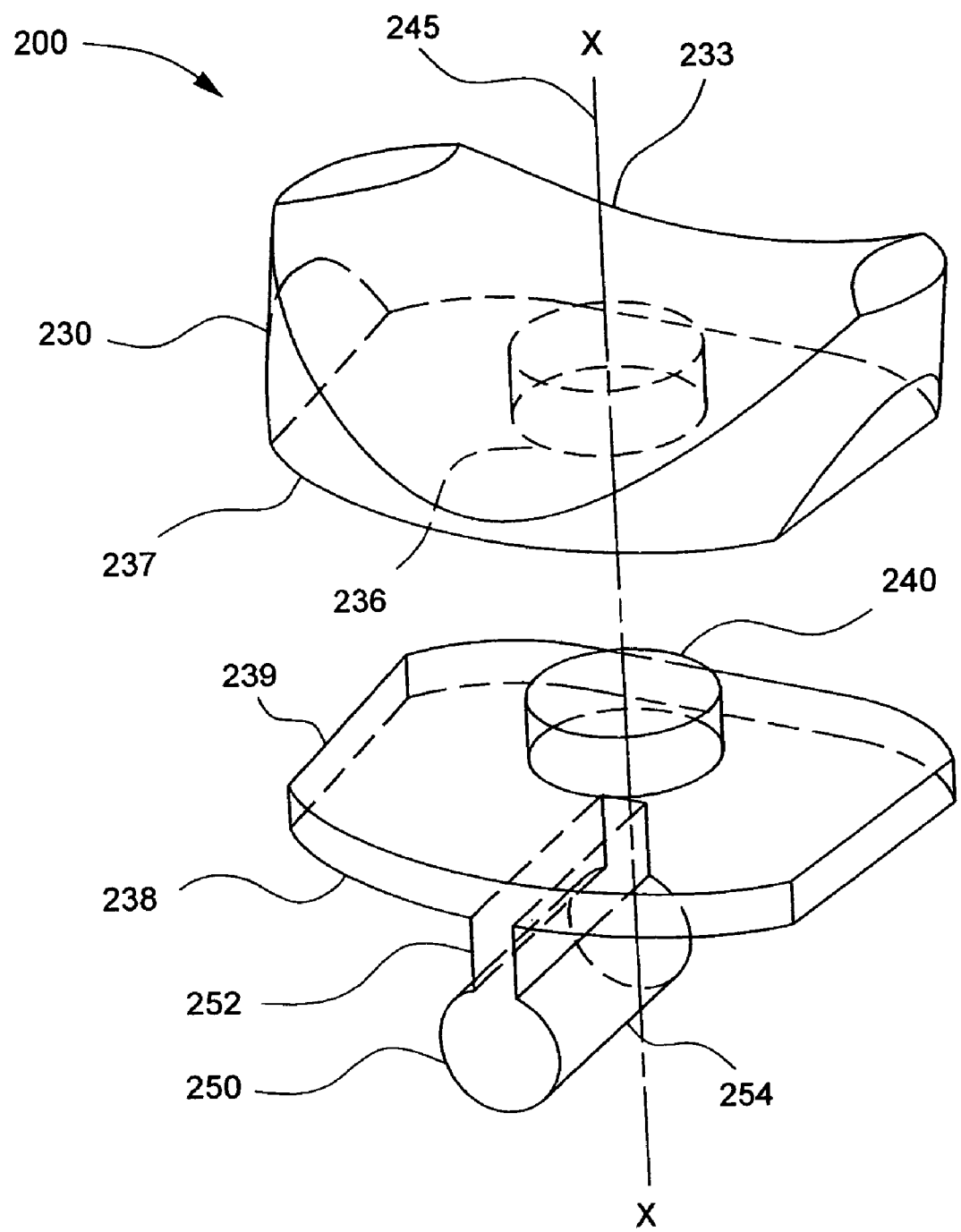
FIG. 8 shows a second preferred embodiment artificial disc of the present invention with a disc body slidably attached to a base plate to permit rotational and translational sliding.

Within the scope of the present invention, multiple components may be allowed to articulate to address multiple degrees-of-freedom associated with spinal motion, to include, but not limited to, torsional and translational degrees-of-freedom. Accordingly, FIG. 8 shows a second preferred embodiment of the present invention, artificial disc 200 in an exploded perspective view. Artificial disc 200 is comprised of a disc body 230, concave-convex articulating surface 233, base plate 238, and bone anchor 250. Bone anchor 250 is comprised of vertical web 252 and anchor body 254. Base plate protrusion 240 inserts into disc body socket 236, while disc body articulating surface 237 and base plate articulating surface 239 allow sliding rotation of disc body 230 about axis X-X 245. Alternately, disc body socket 236 may take various shapes and sizes relative to base plate protrusion 240 to allow planer translation between disc body 230 and base plate 238. For example, disc body socket 236 may take the form of an elongated slot. Although, disc body articulating surface 237 and base plate articulating surface 239 are shown as planer surfaces, curved surfaces are also contemplated. A cylindrical shape for base plate protrusion 240 is shown in FIG. 8, however, other shapes are also envisioned within the scope of the present invention.

Figure 9:
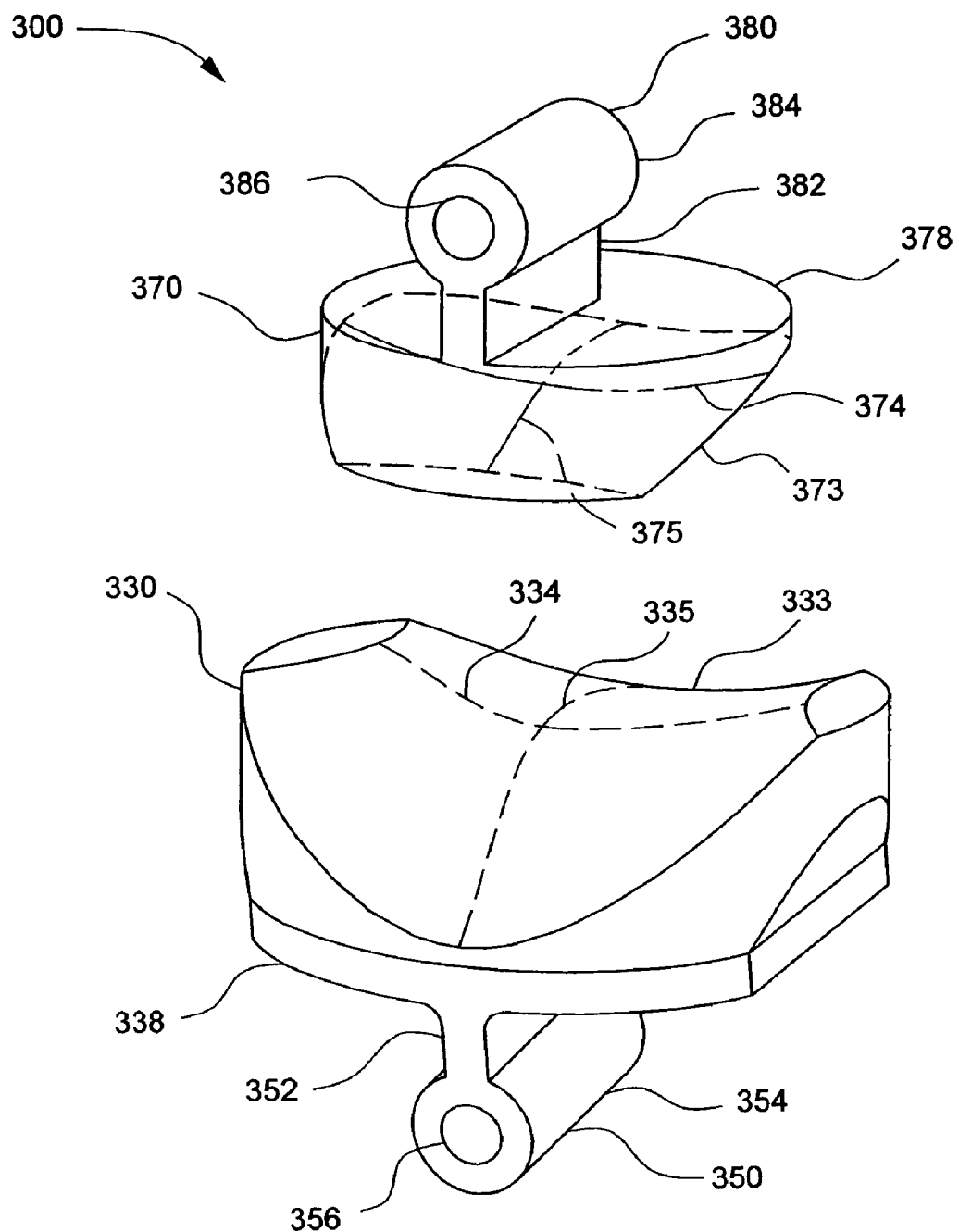
FIG. 9 shows a third preferred embodiment artificial disc of the present invention to include an upper disc body and a lower disc body cooperatively forming a saddle-joint with concave-convex surfaces.

For a number of reasons, to include anatomical variation, the inferior endplate of a superior vertebra may not be suitable as an articulating surface. During treatment of a cervical spine disorders, endplates are often partially or completely removed in order to access and remove offending soft tissue (e.g., extruded disc nucleus) or offending hard tissue (e.g., posterior bone spurs). A total joint artificial disc is often warranted. Accordingly, FIG. 9 shows a third preferred embodiment of the present invention, artificial disc 300, comprised of lower disc body 330 and upper disc body 370. Lower disc body 330, attached to lower base plate 338, has a lower body concave-convex articulating surface 333. Lower bone anchor 350 is comprised of lower vertical web 352 and lower anchor body 354. Upper disc body 370 is comprised of upper base plate 378, upper body concave-convex articulating surface 373, and upper bone anchor 380. Upper bone anchor 380 is comprised of upper vertical web 382 and upper anchor body 384. Lower anchor hole 356 and upper anchor hole 386 can be used to releasably attach a surgical instrument during implantation of artificial disc 300. Lower body concave-convex articulating surface 333 is further defined by concave surface line 334 and midsagittal convex surface line 335. Lower base plate 338 and lower bone anchor 350 are adapted for fixation to an inferior vertebra. Similarly, upper bone anchor 380, comprised of upper vertical anchor web 382 and upper anchor body 384 are adapted for body fixation to a vertebra. The reciprocal reception of lower body concave-convex articulating surface 333 with upper body concave-convex articulating surface 373 forms a saddle-joint. The complement of lower body concave surface line 334 is upper body convex surface line 374, and the complement of lower body convex surface line 335 is upper body concave surface line 375. Surface contours of lower body concave-convex articulating surface 333 and upper body concave-convex articulating surface 373 may be dimensionally matched. Or, surface contours of lower body concave-convex articulating surface 333 and upper body concave-convex articulating surface 373 may be cooperatively aligned, but dimensionally mismatched to give the saddle-joint additional freedom ("toggle") or to establish selected regions of surface contact within manufacturing tolerances. A "gentle braking" occurs in torsion between the lower disc body 330 and the upper disc body 370 as the lower body concave-convex articulating surface 333 and upper body concave-convex articulating surface 373 interact during a torsional motion away from a neutral position, reflecting a more natural resistance to torsional loading. In addition, the surface geometry defining the articulating interaction of lower body concave-convex articulating surface 333 and upper body concave-convex articulating surface 373 may be developed to substantially replicate the complex natural motions of the spine, to include, but not limited to, flexion/extension, lateral bending, and torsional motion.

Figure 10:
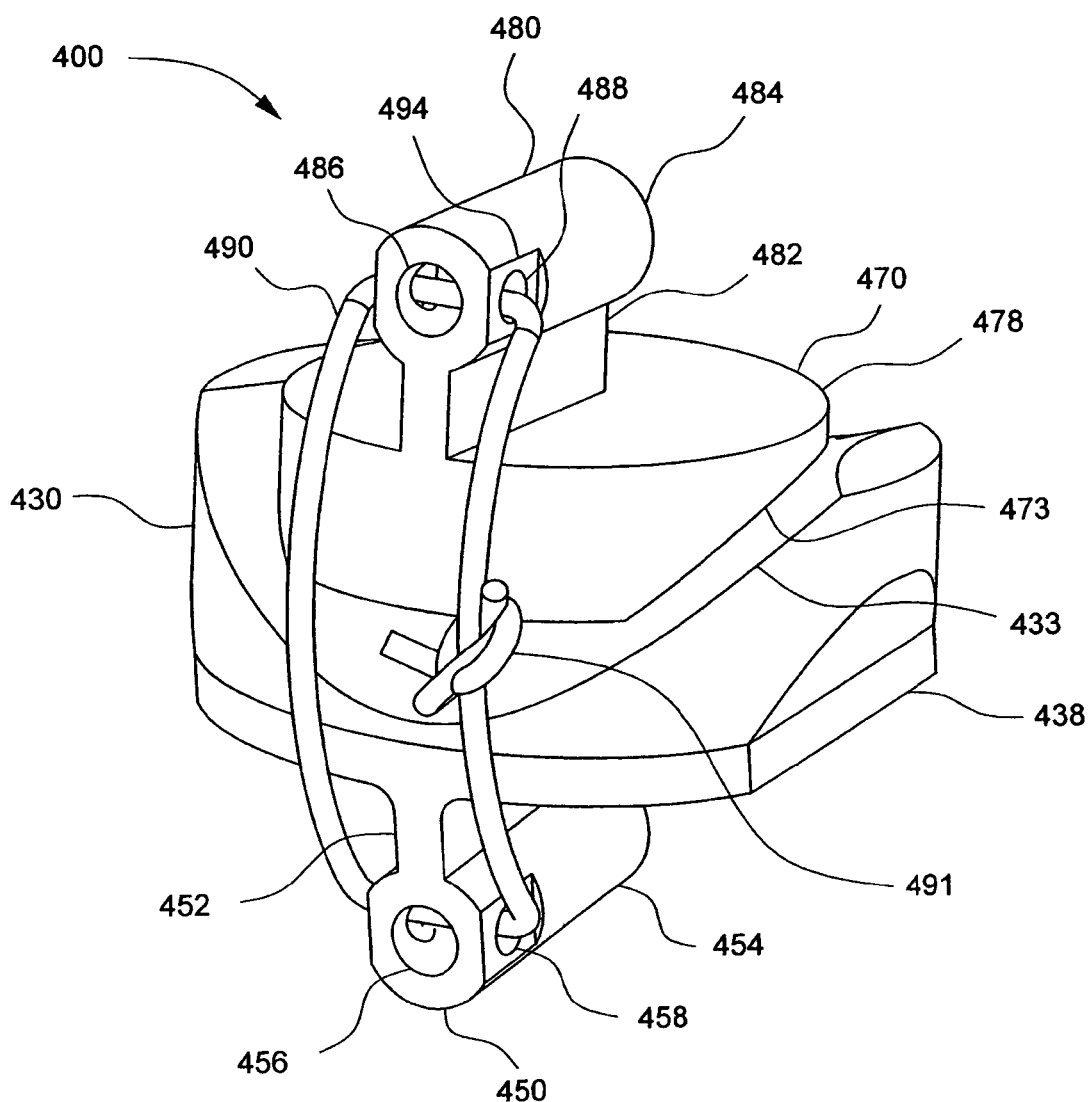
FIG. 10 shows a fourth preferred embodiment artificial disc of the present invention to include an upper disc body and a lower disc body cooperatively forming a saddle-joint with concave-convex surfaces and a tension cable.

Using an anterior approach to the cervical spine, the anterior longitudinal ligament is at least partially resected with associated loss of stability, especially in extension. An artificial disc with a tension element provides stability during extension. Referring now to FIG. 10, a fourth preferred embodiment is shown, artificial disc 400, comprised of lower disc body 430 and upper disc body 470. Lower disc body 430 is joined to lower base plate 438. Lower disc body 430 is also comprised of a lower body concave-convex articulating surface 433. Lower bone anchor 450, comprised of lower vertical web 452 and lower anchor body 454, is adapted for fixation to bone. Upper disc body 470 comprised of upper base plate 478, upper body concave-convex articulating surface 473 and upper bone anchor 480. Upper bone anchor 480 is comprised of upper vertical web 482 and upper anchor body 484. One use of lower anchor hole 456 and upper anchor hole 486 is to releasably attach a surgical instrument during insertion of artificial disc 400. A saddle-joint is formed by the reciprocal reception of lower body concave-convex articulating surface 433 with upper body concave-convex articulating surface 473. Tension cable 490, to include cable knot 491, is secured through the lower anchor eyelet 458 and the upper anchor eyelet 488. Tension cable 490 provides additional stability, restricting motion, especially during extreme extension.

Figure 11:
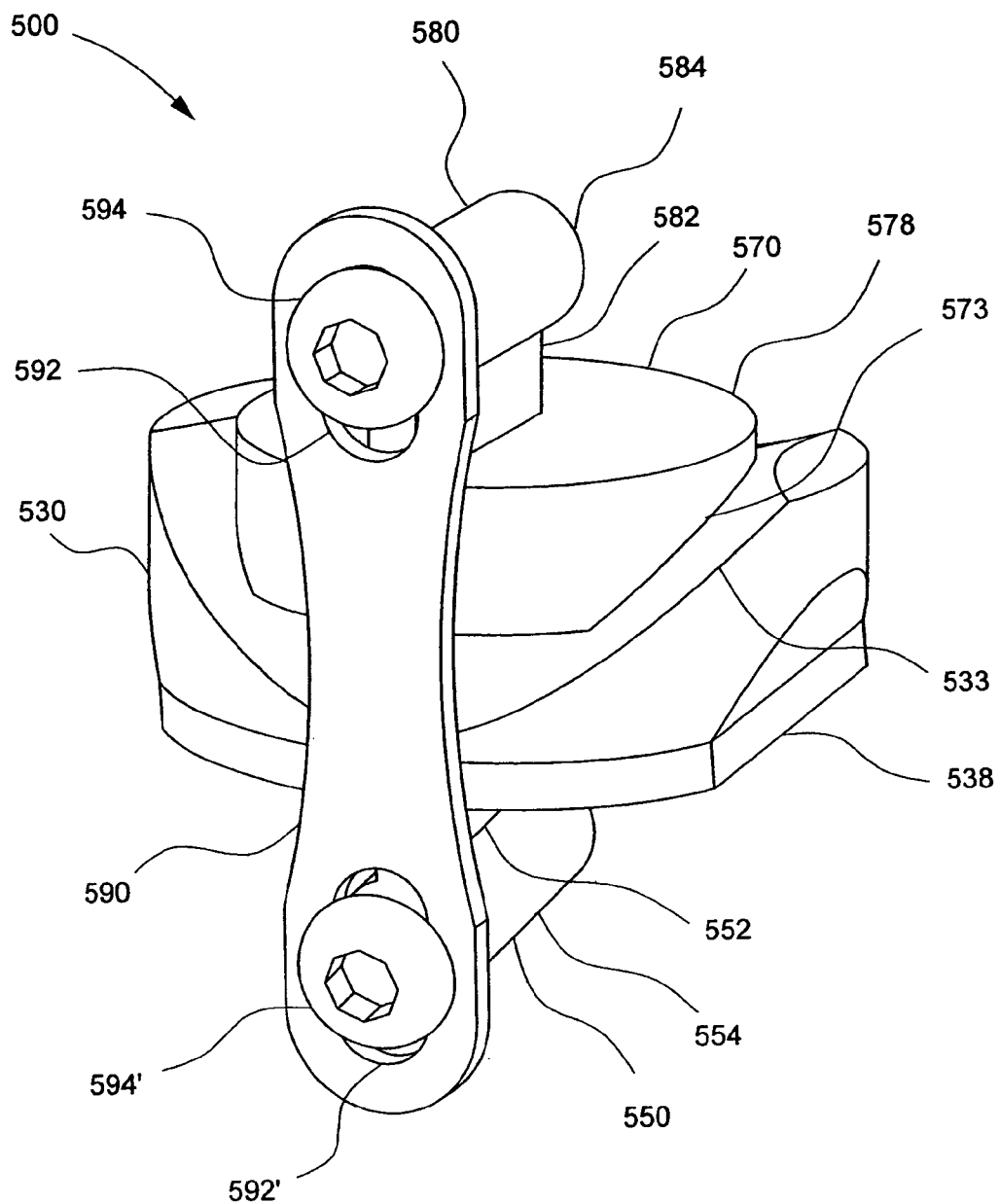
FIG. 11 shows a fifth preferred embodiment artificial disc of the present invention to include an upper disc body and a lower disc body cooperatively forming a saddle-joint with concave-convex surfaces and a flexible plate.

FIG. 11 shows a fifth preferred embodiment, artificial disc 500, comprised of lower disc body 530 and upper disc body 570. Lower disc body 530 includes lower body concave-convex articulating surface 533. Lower disc body 530 is attached to lower base plate 538. Lower bone anchor 550, adapted for interlocking connection to bone, is comprised of lower vertical web 552 and lower anchor body 554. Upper disc body 570 is comprised of upper base plate 578 and upper body concave-convex articulating surface 573. Upper bone anchor 580 is comprised of upper vertical web 582 and upper anchor body 584. The reciprocal reception of lower body concave-convex articulating surface 533 with upper body concave-convex articulating surface 573 forms a saddle-joint. Flexible plate 590 is secured to lower anchor body 550 and upper anchor body 580 by lower fastener 594' and upper fastener 594, respectively. Flexible plate 590 is intended to provide greater stability in extension. To allow specified range-of-motion in extension and flexion where flexible plate 590 is not substantially under load, lower fastener 594' and upper fastener 594 are intended to slide with respect to lower plate slot 592' and upper plate slot 592, respectively.

Figure 12:
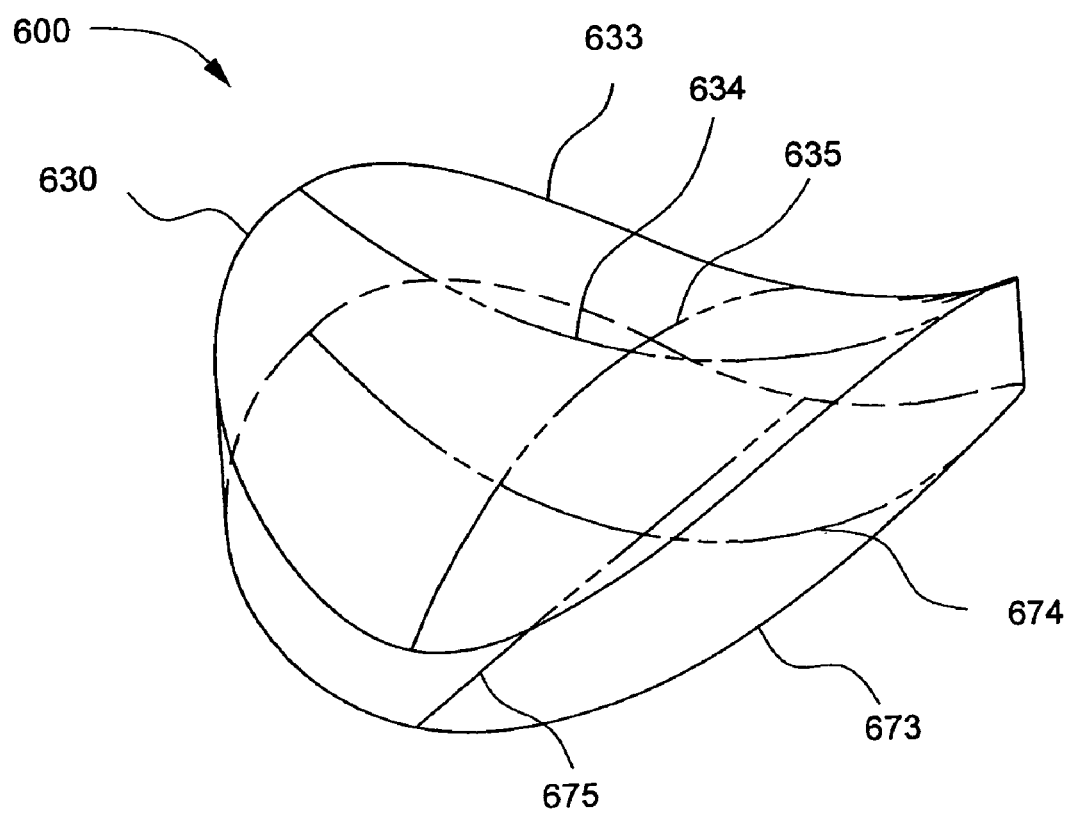
FIG. 12 shows a sixth preferred embodiment artificial disc of the present invention with an upper articulating concave-convex surface and a lower articulating surface.

Within the scope of the current invention, an artificial disc may have an upper articulating surface and a lower articulating surface for sliding interaction with vertebral bodies. FIG. 12 shows a sixth preferred embodiment, artificial disc 600, comprised of disc body 630, upper articulating concave-convex surface 633 and lower articulating surface 673. Curvature of upper articulating concave-convex surface 633 is further defined by concave surface line 634 and midsagittal convex surface line 635. Lower surface line 674 is at least generally convex and lower midsagittal plane surface line 675 is generally straight, but may also have curvature.

The present invention, to include, but not limited to the aforementioned embodiments, can be constructed of established orthopaedic materials. Established wear resistant materials for components with articulating surfaces include metals (e.g., stainless-steel, cobalt-chrome, and titanium), plastics (e.g., Ultra-High-Molecular-Weight-Polyethylene), and ceramics (e.g., alumina and zironia). Non-articulating features of an artificial disc of the present invention may have features or material characteristics to facilitate rigid attachment to bone. An artificial disc of the present invention may be adapted additional features known for attachment to bone including, but not limited to, spikes, screws, serration, and plate-like appendages generally exterior to the intervertebral disc space. Components may be made, in part, constructed of substantially porous materials for bone in-growth, yet have smooth non-porous regions for articulating surfaces. Surface treatments commonly practiced, such as beaded-coatings, may also be used for attachment to bone through eventual bone in-growth. In addition, within the scope of the current invention, components may be given flexibility through the use of geometry and materials to replicate the cushioning characteristics of the natural intervertebral disc. Additional components, such as, springs might be added to provide flexibility. In addition, portions of the patient's annulus may remain intact, such that the present invention augments a patient's existing intervertebral disc. Although the utility of the disclosed artificial disc is best achieved in the cervical region of the spine, adaptations for the thoracic and lumbar regions of the spine are also within the scope and spirit of the present invention.

What is claimed is:

1. A method of providing a prosthetic disc comprising the steps of:
    removing a portion of an intervertebral disc, thereby creating an intervertebral disc space; and
    placing a prosthetic disc substantially within said intervertebral disc space, wherein the prosthetic disc comprises:
        a disc body, having a first surface that is comprised of a single articulating surface and a second surface as abuse adapted for fixation to a first bone, wherein a solely convex reference curve having a substantially uniform radius of curvature is formed when the single articulating surface is intersected with a midsagittal plane, and wherein concave reference curves are formed when the single articulating surface is intersected with planes orthogonal to the midsagittal plane.

2. The method of claim 1, wherein placing includes mating the disc body to a surface of a verterbra.

3. The method of claim 1, wherein the prosthetic disc is shaped to be mated to a second body upon placing within the intervertebral disc space.

4. The method of claim 1, wherein the prosthetic disc is adapted for articulation with a vertebral body.

5. The method of claim 1, wherein placing includes mating the prosthetic disc to a surface of a second artificial body.

* * * * *